(12) United States Patent
Fisher et al.

(10) Patent No.: US 7,175,990 B2
(45) Date of Patent: Feb. 13, 2007

(54) METHOD OF DETERMINING ENDOMETRIAL RECEPTIVITY

(75) Inventors: Susan J. Fisher, San Francisco, CA (US); Olga Genbacev-Krtolica, Los Gatos, CA (US); Akraporn Prakobphol, Folsom, CA (US); Michael T. McMaster, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 79 days.

(21) Appl. No.: 10/374,318

(22) Filed: Feb. 25, 2003

(65) Prior Publication Data

US 2003/0219836 A1 Nov. 27, 2003

Related U.S. Application Data

(60) Provisional application No. 60/360,276, filed on Feb. 26, 2002.

(51) Int. Cl.
*G01N 33/53* (2006.01)

(52) U.S. Cl. .............. 435/7.1; 435/7.92; 424/137.1
(58) Field of Classification Search ............... 435/7.1
See application file for complete search history.

(56) References Cited

U.S. PATENT DOCUMENTS

| 5,279,941 | A | * | 1/1994 | Lessey ................. 435/7.21 |
| 6,169,071 | B1 |  | 1/2001 | Blaschuk et al. |
| 6,277,824 | B1 |  | 8/2001 | Doherty et al. |
| 6,309,843 | B1 |  | 10/2001 | Timms |
| 6,326,352 | B1 |  | 12/2001 | Blaschuk et al. |

OTHER PUBLICATIONS

Spencer et al., "identification and characterization of glycosylation-dependent cell adhesion molecule 1-like protein expression in the ovine uterus," 1999, Biology of Reproduction, 60:241-250.*
Hey et at., "Sialyl-Lewis x and sialyl-Lewis a are associated with MUC1 in human endothelium," 1996, Gylcoconjugate Journal, 13:769-779.*
Holmes et al., "Preparation of cells and reagents for flow cytometry," in Current Protocols in Immunology, 2001, John Wiley & Sons, 5.3.1-5.3.24.*
Frenette et al., Thromb Haemost (1997) 78:60-64.*
Whyte et al., Cell Biol Int (1994) 18:759-766.*
Norwitz et al. (2001) *N. Engl. J. Med.* 345:1400-1408.
Bertozzi and Kiessling (2001) *Science* 291:2357-64.
Rosen (1999) *Am J Pathol* 155:1013-20.
Alon et al. (1997) *J Cell Biol* 138:1169-80.
Alon et al. (1998) *Proc Natl Acad Sci U S A* 95:11631-6.
Gunn et al. (1998) *Proc Natl Acad Sci U S A* 95:258-63.
Carson et al. (2000) *Dev Biol* 223:217-37.
Norwitz et al. (2001) *N Engl J Med* 345:1400-1408.
Damsky and Fisher (1998) *Curr Opin Cell Biol* 10:660-6.
Ilic et al. (2001) *Am J Pathol* 159:93-108.
Drake et al. (2001) *J Exp Med* 193:1199-212.
Guleria and Pollard (2000) *Nat Med* 6:589-93.
Sutherland et al. (1993) *Development* 119:1175-1186.

* cited by examiner

*Primary Examiner*—G. R. Ewoldt
*Assistant Examiner*—Michael Szperka
(74) *Attorney, Agent, or Firm*—Paula A. Borden; Bozicevic, Field & Francis LLP

(57) ABSTRACT

The present invention provides a method of predicting the probability of a successful pregnancy, either a naturally achieved pregnancy or a pregnancy resulting from an assisted reproductive technology, based on the level of L-selectin ligand expressed by uterine epithelial cells and/or the level of L-selectin expressed by an embryo in vitro. The invention further provides methods of inhibiting cell adhesion between a trophoblast and a uterine epithelial cell. Methods of inhibiting cell adhesion between a trophoblast and a uterine epithelial cell are useful to inhibit pregnancy. The invention further provides methods of assessing in vitro embryo quality. The invention further provides methods of predicting the probability of continued success of a pregnancy during the first 16 weeks of gestation.

6 Claims, 7 Drawing Sheets

MECA-79    control (anti-KLH)

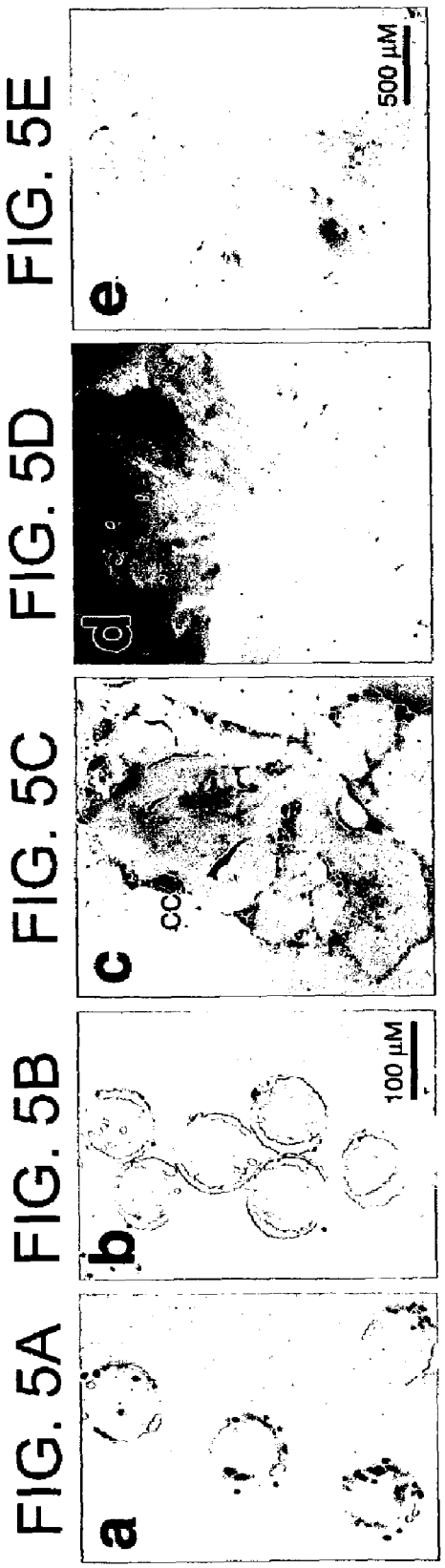

MECA-79 staining

METHOD OF DETERMINING ENDOMETRIAL RECEPTIVITY

CROSS-REFERENCE

This application claims the benefit of U.S. Provisional Patent Application No. 60/360,276, filed Feb. 26, 2002, which application is incorporated herein by reference in its entirety.

STATEMENT REGARDING FEDERALLY SPONSORED RESEARCH

This invention was made with U.S. federal government support under grant nos. DE 07244 and HL 64597 awarded by the National Institutes of Health. The government may have certain rights in this invention.

FIELD OF THE INVENTION

The present invention is in the field of blastocyst implantation and cell adhesion.

BACKGROUND OF THE INVENTION

Leukocytes use specialized mechanisms to emigrate from blood into tissues. Among them are selectins that mediate initial interactions with the vessel wall. These lectin-like protein receptors bind to mucin oligosaccharide ligands that are constitutively expressed in some locations (high endothelial venules) and inducible in others (inflamed endothelia). Selectin receptor-ligand bonds have unusual kinetic and mechanical properties that permit transient tethering and shear stress-dependent rolling. Upon capture, integrin activation triggers stable adhesion, bringing the cells into contact with factors that govern transmigration into tissues (e.g., chemokines and cytokines).

At a morphological level, analogies can be drawn between key steps in leukocyte emigration from blood and embryo attachment to the uterine wall. Implantation begins with apposition: the trophectoderm of the originally free-floating embryo lies adjacent to the uterine epithelium, but the blastocyst is easily dislodged. Soon thereafter, blastocyst adhesion to the uterine wall is stabilized and trophoblasts transmigrate across the uterine epithelium, a process that in humans buries the entire embryo beneath the uterine surface. Subsequent development depends on the ability of trophoblasts to adhere under conditions of shear stress created when these fetal cells breach uterine vessels, a process that diverts maternal blood flow to the placenta. At a molecular level, trophoblast adhesion from implantation onward is an integrin-dependent process that takes place in a chemokine- and cytokine-rich milieu analogous to the blood-vascular interface.

Reproductive failure is a serious problem that has been addressed clinically by various assisted reproductive technologies, including in vitro fertilization (IVF) and embryo transfer (ET). These procedures might be expected to yield exceptionally high conception rates as in vitro fertilization provides embryos that appear normal at a morphological level for transfer into a fully primed recipient. Despite these efforts the success rate of IVF/ET is less than ideal. In the published data for IVF/ET in the United States and Canada in 1994, there were 26,961 initiated cycles of standard IVF. Of these, 86.2% led to retrieval and of these 90.2% led to a transfer. However, the overall success rate in terms of clinical pregnancies was 22.7% per initiated cycle and a 29.1% pregnancy rate per transfer.

Additionally, there appears to be a high incidence of early pregnancy loss after in vitro fertilization with a biochemical pregnancy rate of 18% and a spontaneous abortion rate of 27%. Thus, it appears that the IVF technique has been well optimized but implantation failure may be the cause for a large number of losses with ET and this peri-implantational loss is an area of potential improvement. A major factor in the success rate of various assisted reproductive technologies is endometrial receptivity, a transient state that must be coordinated with embryo development to implantation-competent blastocysts.

Improved methods of contraception, that is prevention of fertilization or implantation of the fertilized egg, are needed particularly in light of increasing population pressure. Many efforts have been made to provide improved contraception utilizing devices or hormonal therapy for females as for example as set forth in U.S. Pat. Nos. 5,771,900; 5,756,115; 5,583,129; 4,922,928; 4,703,752; and 4,564,362 and the references cited therein. However, they are not always successful in providing contraception and improved methods are needed. Progesterone receptor antagonists (such as RU486) alter uterine biochemistry but this alteration is used to induce abortion or as a morning-after pill to prevent implantation. It would be useful to have other methods available that can change uterine receptivity biochemically.

There is a need in the art for methods for determining endometrial receptivity to embryo implantation. There is also a need in the art for additional methods of inhibiting pregnancy. There is also a need in the art for non-invasive methods for evaluating embryo quality prior to transfer in assisted reproductive technologies. There is also a need for markers that identify a woman's relative risk of experiencing a spontaneous abortion early in pregnancy. The present invention addresses these needs.

Literature

U.S. Pat. Nos. 6,309,843; 6,326,352; 6,277,824; and 6,169,071. Norwitz et al. (2001) *N. Engl. J. Med.* 345: 1400–1408; Bertozzi and Kiessling (2001) *Science* 291: 2357–64; Rosen (1999) *Am J Pathol* 155:1013–20; Alon et al. (1997) *J Cell Biol* 138:1169–80; Alon et al. (1998) *Proc Natl Acad Sci USA* 95:11631–6; Gunn et al. (1998) *Proc Natl Acad Sci USA* 95:258–63; Carson et al. (2000) *Dev Biol* 223:217–37; Norwitz et al. (2001) *N Engl J Med* 345: 1400–1408; Damsky and Fisher (1998) *Curr Opin Cell Biol* 10:660–6; Ilic et al. (2001) *Am J Pathol* 159:93–108; Sutherland et al. (1993) *Development* 119:1175–1186; Drake et al. (2001) *J Exp Med* 193:1199–212; Guleria and Pollard (2000) *Nat Med* 6:589–93.

SUMMARY OF THE INVENTION

The present invention provides a method of predicting the probability of a successful pregnancy, either a naturally achieved pregnancy or a pregnancy resulting from an assisted reproductive technology, based on the level of L-selectin ligand expressed by uterine epithelial cells and/or the level of L-selectin expressed by an embryo in vitro. The invention further provides methods of inhibiting cell adhesion between a trophoblast and a uterine epithelial cell. Methods of inhibiting cell adhesion between a trophoblast and a uterine epithelial cell are useful to inhibit pregnancy. The invention further provides methods of assessing in vitro embryo quality. The invention further provides methods of predicting the probability of continued success of a pregnancy during the first 16 weeks of gestation.

Features of the Invention

The present invention provides methods of determining the probability of success of implantation following an assisted reproductive technology or naturally achieved conception. The methods generally involve determining the level of an L-selectin ligand produced by a uterine epithelial cell in a biological sample; comparing the level to a standard; and determining the probability of success of implantation following an assisted reproductive technology or naturally achieved conception based on the level of L-selectin ligand produced by the uterine epithelial cell. Suitable biological samples include, but are not limited to, a uterine biopsy sample, a uterine fluid sample, a vaginal fluid sample, saliva, and maternal blood. Assisted reproductive technologies for which the subject methods find use include, but are not limited to, in vitro fertilization, embryo transfer, gamete intrafallopian transfer, tubal embryo transfer, intracytoplasmic sperm injection, and intrauterine insemination.

The L-selectin ligand is detected using a binding agent specific for L-selectin. In some embodiments, the binding agent is detectably labeled. In some embodiments, the L-selectin is detected using an immunological assay and the binding agent is an antibody specific for the L-selectin ligand. In some of these embodiments, the antibody is MECA-79. In some embodiments, the binding agent is an L-selectin. In some embodiments, the binding agent is a fusion protein comprising an L-selectin.

The invention further provides methods of inhibiting binding between an L-selectin ligand on a uterine epithelial cell and an L-selectin on a trophoblast. The methods generally involve contacting said trophoblast and said uterine epithelial cell with an agent that inhibits binding of the L-selectin to the L-selectin ligand. In some embodiments, the agent is an antibody specific for the L-selectin. In some embodiments, the agent is an antibody specific for the L-selectin ligand.

The invention further provides methods of inhibiting binding between an L-selectin ligand on a uterine epithelial cell and an L-selectin on a trophoblast. The methods generally involve contacting said uterine epithelial cell with an agent that inhibits a sulfotransferase that sulfates the L-selectin ligand.

The invention further provides methods of inhibiting pregnancy in a female mammal. The method generally comprise administering to the mammal an agent that inhibits binding between an L-selectin ligand on a uterine epithelial cell and an L-selectin on a trophoblast.

The invention further provides methods of assessing the likelihood that an in vitro embryo will implant into the uterine wall when transferred into the uterus of a female mammal. The methods generally involve determining the level of L-selectin produced by a trophoblast of the embryo. The level of L-selectin is determined using a binding agent specific for an L-selectin. In some embodiments, the binding agent is an L-selectin ligand. In other embodiments, the binding agent is an antibody specific for L-selectin.

The invention further provides methods of determining the probability of success of implantation of an in vitro embryo following an assisted reproductive technology. The methods generally involve determining the amount of L-selectin produced by a trophoblast of the in vitro embryo before implantation; comparing the level to a normal level; and determining the probability of success of implantation following an assisted reproductive technology based on the level of L-selectin produced by a trophoblast of the embryo.

The invention further provides methods of determining the probability of continued success of a pregnancy during the first 16 weeks following conception. The methods generally involve determining the level of L-selectin in a biological sample from the pregnant female during the first 16 weeks of pregnancy; comparing the level to a normal level; and determining the probability of continued success of the pregnancy based on the level of L-selectin produced by a trophoblast of the embryo.

BRIEF DESCRIPTION OF THE DRAWINGS

FIGS. 5A–E depict results showing that trophoblasts bind oligosaccharide ligands through L-selectin. CC, cytotrophoblast column.

DEFINITIONS

Figure 1A:
FIGS. 1A–O depict results showing that receptive human and murine uterine epithelial cells express sulfated selectin oligosaccharide ligands in situ. LE, luminal epithelium; GE glandular epithelium.
Figure 1B:
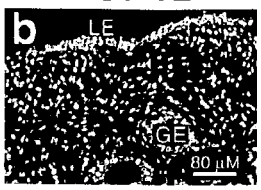

The term "assisted reproductive technology" refers to technology that assists in achieving pregnancy, including, but not limited to, in vitro fertilization (IVF), embryo transfer (e.g., transfer of embryos at any stage, including blastocysts), gamete intrafallopian transfer (GIFT), tubal embryo transfer (TET), intracytoplasmic sperm injection (ICSI) and intrauterine insemination (IUI).

As used herein, the term "abnormal levels of L-selectin ligand" includes higher than normal levels of L-selectin ligand, lower than normal levels of L-selectin ligand, abnormal spatial expression of L-selectin ligand, and abnormal temporal expression of L-selectin ligand. In particular embodiments, "abnormal levels" of L-selectin ligand refers to lower than normal levels of L-selectin ligand.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polysaccharides, glycoproteins, or proteins. The term "biological sample" encompasses a clinical sample, and also includes cells in culture, cell supernatants, cell lysates, saliva, blood, serum, plasma, biological fluid (e.g., cervical fluid, vaginal fluid), and tissue samples.

As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be delectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity," in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens.

The term "detectably labeled antibody," refers to an antibody (or antibody fragment which retains binding specificity for an L-selectin, an L-selectin ligand, or epitope of an L-selectin or L-selectin ligand), having an attached detectable label. The detectable label is normally attached by chemical conjugation, but where the label is a polypeptide, it could alternatively be attached by genetic engineering techniques. Methods for production of delectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

The terms "individual" and "patient" are used interchangeably herein to refer to a female mammal, including, but not limited to, murines, simians, humans, felines, canines, equines, bovines, mammalian farm animals, mammalian sport animals, and mammalian pets. Of particular interest in many embodiments are human females. The term "embryo" refers to mammalian embryos, including human embryos.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an L-selectin ligand" includes a plurality of such ligands and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the observations that uterine expression of specialized carbohydrate structures that support selectin-mediated adherence is dramatically upregulated as the uterus becomes receptive to implantation; and that trophoblasts express L-selectin, which mediates binding to the selectin ligands expressed on the surface of uterine epithelial cells.

The present invention provides diagnostic assay methods for determining the time of optimal uterine receptivity toward blastocyst implantation. The methods generally involve determining the level of L-selectin ligand produced by uterine epithelial cells. Based on the level of L-selectin ligand produced by uterine epithelial cells, compared to a standard, the probability of success of implantation is determined. Determination of the optimal time period for implantation increases the chance that implantation will be successful. Determination of the optimal time period for implantation is of particular importance in techniques such as in vitro fertilization (IVF), embryo transfer, gamete intrafallopian transfer (GIFT), tubal embryo transfer (TET), intracytoplasmic sperm injection (ICSI) and intrauterine insemination (IUI). The present methods provide for monitoring a hormonal regimen in patients undergoing IVF, to determine the time of optimal uterine receptivity. Detection of defects in uterine preparation, such as luteal phase defects in which the uterine lining is out of phase with embryonic development, is diagnosed by assessing L-selectin ligand expression by uterine epithelial cells.

The present invention further provides methods of diagnosing infertility, where the infertility is related to or caused by abnormal levels of L-selectin ligand.

The invention further provides methods for assessing embryo quality in an assisted reproductive technology by monitoring L-selectin production by the embryo.

The invention further provides methods for predicting the risk of spontaneous abortion once pregnancy is established, e.g., within the first 16 weeks of pregnancy, by monitoring L-selectin ligand levels in maternal blood or uterine and/or cervical secretions.

The present invention further provides methods of performing perimenopausal evaluation of a female individual, the method involving monitoring L-selectin ligand levels in the individual.

The present invention further provides methods of preventing or inhibiting implantation of a blastocyst in the uterine wall. The methods generally involve administering to an individual an agent that inhibits binding of an L-selectin on the surface of a trophoblast to an L-selectin ligand on the surface of a uterine epithelial cell.

Methods of Determining Uterine Receptivity to Blastocyst Implantation

The present invention provides a method of determining uterine receptivity to blastocyst implantation. The methods generally involve determining a level in a patient of L-selectin ligand or MECA-79 antigen produced by a uterine epithelial cell of an individual; comparing the determined level to a standard level; and determining the probability of success of implantation following a naturally achieved pregnancy or following an assisted reproductive technology based on the comparison; wherein the L-selectin ligand or MECA-70 antigen level is determined from a biological sample obtained from the patient, e.g., a uterine biopsy specimen; vaginal secretion; uterine secretion; blood (or a blood fraction such as serum); and saliva. The methods are useful in determining the optimal timing for a naturally achieved pregnancy (e.g., implantation following naturally achieved conception), or a pregnancy achieved with an assisted reproductive technology. Thus, the instant invention provides methods of determining a probability of success with an assisted reproductive technology as well as methods of determining the probability of implantation following a naturally achieved conception.

L-selectin ligands that produced by a uterine epithelial cell are detected in a biological sample from the individual. Suitable biological samples include, but are not limited to, uterine secretions; cervical secretions; endometrial biopsy samples; maternal blood; and saliva.

The level of L-selectin ligand is compared to a non-receptive control. In normal fertile human female controls, L-selectin ligands are present on the surface of luminal and glandular uterine epithelial cells between day 14 (where ovulation occurs) and day 19 of a menstrual cycle, with the level of expression being the highest toward day 19. The highest level of expression of L-selectin ligands on uterine epithelial cells may vary somewhat from individual to individual. Accordingly, in general, a standard curve is generated for an individual over a complete menstrual cycle to determine the time point at which the level of L-selectin ligand produced by uterine epithelial cells is highest for that individual. Where necessary for the evaluation, repetitive samples will be collected throughout the menstrual cycle. Non-receptive controls are both women who are in the non-fertile stage of the menstrual cycle and women with known uterine dysfunction where L-selectin ligand levels are low or absent from uterine epithelial cells throughout the menstrual cycle.

L-selectins that are expressed on the surface of lymphocytes are known in the art. For example, human L-selectin cDNA and protein sequences are provided in GenBank Accession No. AJ246000. L-selectin ligands that are known in the art and that are expressed on cells such as vascular endothelial cells include, but are not limited to, GlyCAM-1, CD34, MAdCAM-1, Sgp200, podocalyxin, endoglycan, PSGL-1, and L-selectin-binding fragments thereof.

L-selectin ligands that are expressed on the surface of uterine epithelial cells and that interact with L-selectin on the surface of a trophoblast generally include one or more of the following carbohydrate epitopes: $SO_3{\rightarrow}6GlcNAc$; $sLe^x$ ($Sia\alpha2{\rightarrow}3Gal\beta1{\rightarrow}4[Fuc\alpha1{\rightarrow}3]GlcNAc$); 6-sulfo $sLe^x$ ($Sia\alpha2{\rightarrow}3Gal\beta1{\rightarrow}4[Fuc\alpha1{\rightarrow}3][SO_3{\rightarrow}6]GlcNAc$), 6'-sulfo $sLe^x$ ($Sia\alpha2{\rightarrow}3[SO_3{\rightarrow}6]Gal\beta1{\rightarrow}4[Fuc\alpha1{\rightarrow}3]GlcNAc$); and 6',6-disulfo $sLe^x$ ($Sia\alpha2{\rightarrow}3[SO_3{\rightarrow}6]Gal\beta1{\rightarrow}4[Fuc\alpha1{\rightarrow}3][SO_3{\rightarrow}6]GlcNAc$); 6-sulfo $sLe^x$ on entended core-1, ($Sia\alpha2{\rightarrow}3Gal\beta1{\rightarrow}4[Fuc\alpha1{\rightarrow}3]$ $(SO_4\text{-}6)$ $GlcNAc\beta1{\rightarrow}3Gal\beta1{\rightarrow}3GalNAc$.

L-selectin ligands produced by uterine epithelial cells are detected in a biological from the individual (e.g., uterine fluid sample, vaginal fluid sample, uterine biopsy, blood or blood fraction, saliva, etc.) using any known method. Generally, a binding agent specific for an L-selectin ligand is used. Binding agents specific for an L-selectin ligand include antibodies, L-selectins, and recombinant agents that include either an antibody specific for an L-selectin ligand or an L-selectin. L-selectin ligands that are suitable for use herein include, but are not limited to, a mucin, GlyCAM-1, CD34, MAdCAM-1, Sgp200, endoglycan, PSGL-1, and L-selectin-binding fragments thereof. Antibodies specific for L-selectin ligands include, but are not limited to, MECA-79, HECA-452, CSLEX, G72, G152, and PEN5. G72 and G152 are described in, e.g., Mitsuoka et al. (1998) *J. Biol. Chem.* 273:11225–11233. In some embodiments, a binding agent is detectably labeled, either directly or indirectly. In some embodiments, a binding agent is bound to an insoluble support.

In some embodiments, a recombinant binding agent, e.g., a fusion protein, is used, in which the fusion protein comprises an L-selectin or an antibody specific for an L-selectin ligand, and a fusion partner. Suitable fusion partners include, but are not limited to, where suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; antibodies and antibody fragments; polypeptides that facilitate purification or isolation of the fusion protein, e.g., metal ion binding polypeptides such as 6His tags, GST, and the like. Fluorescent proteins include, but are not limited to, a green fluorescent protein from *Aequoria victoria* or a mutant or derivative thereof e.g., as described in U.S. Pat. Nos. 6,066, 476; 6,020,192; 5,985,577; 5,976,796; 5,968,750; 5,968, 738; 5,958,713; 5,919,445; 5,874,304; e.g., Enhanced GFP, many such GFP which are available commercially, e.g., from Clontech, Inc.; any of a variety of fluorescent and colored proteins from *Anthozoan* species, as described in, e.g., Matz et al. (1999) *Nature Biotechnol.* 17:969–973; and the like. One non-limiting example of a suitable fusion protein is an L-selectin-IgG fusion protein.

The binding agent can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982.) The binding of antibodies and other molecules to a solid support substrate is also well known in the art. (see for a general discussion Harlow & Lane Antibodies: A Laboratory Manual, Cold Spring Harbor Laboratory Publications, New York, 1988).

A binding agent may be attached, directly or indirectly (e.g., via a linker molecule) to a solid support for use in a diagnostic assay to determine and/or measure the presence of L-selectin ligand in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an enzyme linked immunosorbent assay (ELISA) or radioimmunoassay (RIA), and the like); sheets, e.g., nylon, nitrocellulose, and the like, which may be in the form of test strips; and chips, e.g., $SiO_2$ chips such as those used in microarrays. Accordingly, the invention further provides assay devices comprising a binding agent attached to a solid support.

The detection methods may be designed a number of different ways, where a variety of assay configurations and protocols may be employed, as are known in the art. For example, one of the components, e.g., an antibody to an L-selectin ligand, may be bound to a solid support, and the remaining components contacted with the support bound component. The components of the method may be combined at substantially the same time or at different times. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound L-selectin-ligand complexes will then be detected.

Where the detection method is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc., that are used to facilitate optimal protein-protein binding, protein-carbohydrate binding, and/or reduce non-specific or background interactions. Reagents that improve the efficiency of the assay, such as protease inhibitors, nuclease inhibitors, antimicrobial agents, etc. may be used.

Suitable detectable moieties include, but are not limited to, fluorescent, metallic, enzymatic and radioactive markers such as fluorescent proteins, biotin, gold, ferritin, alkaline phosphatase, β-galactosidase, luciferase, horse radish peroxidase, peroxidase, urease, fluorescein, rhodamine, tritium, $^{14}C$, and iodination. The binding agent, e.g., an antibody, can be used as a fusion protein, where the fusion partner is a fluorescent protein. Fluorescent proteins include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; any of a variety of fluorescent and colored proteins from Anthozoan species, as described in, e.g., Matz et al. (1999) *Nature Biotechnol.* 17:969–973; and the like.

Methods Involving Detection of L-Selectin Produced by a Trophoblast

The invention further provides methods of assessing embryo quality, involving determining the level of L-selectin produced by the embryo. Thus, the invention provides a method of assessing the likelihood of that an in vitro embryo will implant into the uterine wall when transferred into the uterus of a female mammal. The method generally comprises determining the level of L-selectin produced by a trophoblast of the embryo. Thus, the invention provides a method of determining the probability of success of implantation of an in vitro embryo following an assisted reproductive technology, the method generally involving determining the amount of L-selectin produced by a trophoblast of the in vitro embryo before implantation (i.e; in vitro); comparing the level to a normal level; and determining the probability of success of implantation following an assisted reproductive technology based on the level of L-selectin produced by the embryo. In some embodiments, L-selectin is detected in culture medium surrounding the embryo. In other embodiments, L-selectin is detected on the embryo itself. A level of L-selectin in the culture medium or on the embryo itself that is in a normal range, i.e., when compared to a normal control(s), indicates that the embryo is suitable for use in an assisted reproductive technology.

An L-selectin is detected using a binding agent that specifically binds L-selectin. In some embodiments, a binding agent is an L-selectin ligand. In other embodiments, a binding agent is an antibody specific for L-selectin. The binding agent may be detectably labeled, directly or indirectly, as discussed above. Antibodies specific for L-selectin include, but are not limited to, DREG-56, C-19, and the like. A binding agent can be detectably labeled, as described above, and/or bound to an insoluble support, using well-known methods. L-selectin ligands that can be detectably labeled and used to detect L-selectin include, but are not limited to, a mucin, GlyCAM-1, CD34, MAdCAM-1, Sgp200, podocalyxin, and L-selectin-binding fragments thereof. Detection methods are as described above.

The invention further provides methods of assessing the risk of spontaneous abortion following a naturally achieved pregnancy, or following an assisted reproductive technology procedure, particularly during the first 16 weeks of gestation. The methods generally involve determining the level of L-selectin in a biological sample from the pregnant female. Suitable biological samples include, but are not limited to, uterine secretion, a cervical secretion, and maternal blood. An abnormal level of L-selectin in the biological sample compared to a normal control indicates a risk (e.g., a higher probability) that the pregnancy will be lost during the first 16 weeks. A level of L-selectin in the biological sample that is within a normal range when compared to a normal control(s) indicates a higher probability that the pregnancy will continue during the first 16 weeks of pregnancy and will not spontaneously abort. L-selectin levels are determined as described above.

Methods of Inhibiting Adhesion of a Trophoblast to a Uterine Epithelial Cell

The present invention provides methods and kits for preventing or inhibiting pregnancy in a female mammal. In general, disruption of interaction (adhesion) between trophoblast L-selectin and L-selectin ligand on a uterine epithelial cell prevents the adhesion of trophoblasts to uterine epithelial cells, and therefore prevents implantation.

Agents that inhibit binding of an L-selectin on a trophoblast to an L-selectin ligand on a uterine epithelial cell include, but are not limited to, an antibody specific for an L-selectin ligand; an antibody specific for an L-selectin; an agent that inhibits a sulfotransferase that sulfates an L-selectin ligand; a small molecule that inhibits binding of trophoblast L-selectin to an L-selectin ligand on the surface of a uterine epithelial cell; and the like.

Sulfotransferases that sulfate an L-selectin ligand include, but are not limited to, HEC-GlcNAc6ST (also referred to as GST-3) (WO 99/49018); KSGal6ST (also referred to as KSST) (EP 821 066; and Fukuta et al. (1997) *J. Biol. Chem.* (1997) 272: 32321–32328); human chondroitin-6-sulfotransferase (C6ST, specificity for C-6 of GalNAc, Fukuta, et al. (1998) *Biochim. Biophys. Acta.* 1399:57–61); GlcNAc-6-sulfotransferase (GlcNAc6ST) (Uchimura et al. (1998) *J. Biochem* (Tokyo) (1998) 124:670–678); I-GlcNAc6ST (Lee et al., *Biochem Biophys Res. Commun* (1999) 263: 543–9; and C-GlcNAc6ST Akama et al. (2000) *Nat. Genet.* 26:237–41.

Agents

The invention further provides agents that inhibit binding of an L-selectin on a trophoblast to an L-selectin ligand on the surface of a uterine epithelial cell. The invention provides formulations, including pharmaceutical formulations, comprising an agent that inhibits binding of an L-selectin on a trophoblast to an L-selectin ligand on the surface of a uterine epithelial cell. In general, a formulation comprises an effective amount of an agent that inhibits binding of an L-selectin on a trophoblast to an L-selectin ligand on the surface of a uterine epithelial cell. An "effective amount" means a dosage sufficient to produce a desired result, e.g., a reduction in binding of an L-selectin on a trophoblast to an L-selectin ligand on the surface of a uterine epithelial cell; and inhibition of pregnancy.

Formulations

In the subject methods, the active agent(s) may be administered to the host using any convenient means capable of resulting in the desired inhibition of binding of an L-selectin on a trophoblast to an L-selectin ligand on the surface of a uterine epithelial cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semisolid, liquid or gaseous forms, such as tablets, capsules, powders, granules, ointments, solutions, suppositories, transdermal patches, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral, vaginal, or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

In one embodiment, one or more agents as described herein may be incorporated into any of a variety of well-known contraceptive devices, such as sponges suitable for intravaginal insertion (see, e.g., U.S. Pat. No. 5,417,224) or capsules for subdermal implantation. Other modes of administration are possible, however, including transdermal administration, oral administration, intrauterine devices, and vaginal suppository. Suitable methods for incorporation into a contraceptive device depend upon the type of device and are well known in the art. Such devices facilitate administration of the agent to the uterine region and may provide a sustained release of the agent. In general, agents may be administered via such a contraceptive device at a dosage ranging from 0.1 to 20 mg/kg. Kits for preventing pregnancy generally comprise a contraceptive device impregnated with one or more agents described herein.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on various factors, a suitable dosage range is one which provides up to about 1 µg to about 1,000 µg or about 10,000 µg of an agent that inhibits binding of an L-selectin on a trophoblast to an L-selectin ligand on the surface of a uterine epithelial cell can be administered in a single dose. The dosage provides for the agent (in one or multiple dosing events) in an effective amount. An effective amount of the agent is an amount that effectively inhibits pregnancy. Whether pregnancy is inhibited is readily determined using well-known methods.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that inhibits binding of an L-selectin on a trophoblast to an L-selectin ligand on the surface of a uterine epithelial cell is administered to an individual using any available method and route suitable for drug delivery, including in vivo and ex vivo methods, as well as systemic and localized routes of administration.

The agent can be administered to a host using any available conventional methods and routes suitable for delivery of conventional drugs, including systemic or localized routes. Conventional and pharmaceutically acceptable routes of administration include intramuscular, transdermal, subcutaneous, vaginal, oral, subcutaneous, intradermal, topical application, intravenous, rectal, vaginal, uterine (as in an intrauterine device), nasal, oral and other parenteral routes of administration. Routes of administration may be combined, if desired, or adjusted depending upon the agent and/or the desired effect. The composition can be administered in a single dose or in multiple doses.

The agent can also be delivered to the subject by enteral administration. Enteral routes of administration include, but are not necessarily limited to, oral, vaginal, uterine, and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Kits with unit doses of the active agent, e.g. in oral, transdermal, or injectable doses, are provided. In such kits, in addition to the containers containing the unit doses will be an informational package insert describing the use and attendant benefits of the drugs in treating pathological condition of interest. Preferred compounds and unit doses are those described herein above.

Kits

The present invention further provides kits for use in a subject method, including kits for detecting L-selectin ligands produced on the surface of uterine epithelial cells; and kits for detecting L-selectin produced by trophoblasts.

A kit for detecting an L-selectin ligand in a biological sample, such as uterine secretion, vaginal secretion, maternal blood, saliva, or uterine biopsy, includes a binding agent that binds specifically to the L-selectin ligand. In some embodiments, the binding agent is detectably labeled. In some embodiments, the kit includes at least two binding agents specific for an L-selectin ligand, wherein one binding agent is not labeled and is bound to an insoluble support, and the second binding agent is detectably labeled. The binding agent(s) is present in a suitable storage medium, e.g., buffered solution, typically in a suitable container. As discussed above, a binding agent may be bound to an insoluble support.

A kit for detecting L-selectin in a biological sample, such as maternal blood, uterine secretion, vaginal secretion, or an in vitro embryo, includes a binding agent that binds specifically to L-selectin. In some embodiments, the binding agent is detectably labeled. In some embodiments, the kit includes at least two binding agents specific for an L-selectin, wherein one binding agent is not labeled and is bound to an insoluble support, and the second binding agent is detectably labeled. The binding agent(s) is present in a suitable storage medium, e.g., buffered solution, typically in a suitable container. As discussed above, a binding agent may be bound to an insoluble support.

A subject kit may further include reagents for solubilizing a macromolecule from a cell membrane, buffers, washing solutions, reagents for developing a signal (e.g., from a detectably labeled binding agent), and the like.

A subject kit may further include reagents for detecting the presence or measuring the level of other components of the biological sample, including, but not limited to, a hormone, including, but not limited to, human chorionic gonadotropin, progesterone, and the like (see, e.g., Norwitz et al. supra); and any placental product, including, but not limited to, HLA-G (a soluble class I MHC molecule).

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disc (CD), etc., on which the information has been recorded. The information may be recorded on a digital versatile disk (DVD), audio cassette, video cassette, or other recording media. Yet another means that may be present is a website address which may be used via the internet to access the information at a remote site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., h, hour(s); sec, second(s); min, minute(s); etc.

Example 1

Expression of L-selectin on Trophoblasts, and L-selectin Ligands on Uterine Epithelium Methods Tissue, Cell and Embryo Sources Samples of the human maternal-fetal interface were from pregnancy terminations (nonmedical reasons) and uncomplicated deliveries. Villus explants and cytotrophoblasts were isolated and cultured on Matrigel as described. Genbacev et al. (1992) *Placenta* 13, 439–61; Librach et al. (1991) *J Cell Biol* 113:437–49. Endometrial biopsies were from women undergoing stimulated cycles for oocyte donation (11 donors) and natural cycles (1 donor). Phase of the menstrual cycle was confirmed by measuring plasma progesterone and estradiol. Biopsies were taken during the nonreceptive phase (day 6) and after ovulation (days 14–20). Three women (2 oocyte donors; 1 natural cycle donor) were biopsied every day for 6 days starting on the day of ovulation. Human neutrophil isolation and Jurkat cell culture were as described. Prakobphol et al. (1999) *Biochemistry* 38: 6817–6825 (1999). Mouse blastocysts (ICR strain) were flushed from uterine horns on day 4 after mating. Some were hatched in 4-well plates (6 embryos/well) containing CMRL Medium-1066 (Life Technologies) and 10% fetal bovine serum. Mouse uteri were removed on days 1 and 4 of the cycle.

Immunolocalization

Immunolocalization methods were as published. Ilic et al. (2001) *Am. J. Pathol.* 159:93–108. Antibodies were diluted 10 µg/ml in PBS. L-selectin expression by human cells was analyzed with FITC-conjugated DREG-56 (Caltag). As a control, purified FITC-conjugated mouse IgG-1 (Caltag) was substituted for DREG-56. Alternatively an antibody to the carboxyl terminus of the molecule (C-19; Santa Cruz Biotechnology) was used for this purpose. For in situ expression, sections of first- (n=20; 6–12 weeks), second- (n=17; 16–22 weeks) and third-trimester placentas (n=5; 36–38 weeks) were analyzed in 11 experiments. For in vitro expression, sections of villus explants (n=24 from 6–8 week placentas in 6 experiments) cultured for 24, 48 and 72 h, purified cytotrophoblasts (n=10; 5–7 placentas of 8–11 weeks) cultured for 24 to 72 h, and Jurkat cells were analyzed. L-selectin expression by mouse cells was assessed with FITC-conjugated MEL-14 (Caltag). As a negative control, a purified FITC-conjugated rat IgG-2a (Caltag) was substituted for MEL-14. Some mouse blastocysts (n=25; 5 experiments) were incubated on ice with anti-L-selectin for 1 h, then fixed in 3.8% paraformaldehyde. Others (n=15; 5 experiments) were fixed and permeabilized (5 min in 0.1% Triton X-100) before staining. Human trophoblast E- and P-selectin expression in situ was analyzed with antibodies from R&D Systems in 6 experiments.

Uterine expression of L-selectin oligosaccharide ligands was assessed using the same methods as above, but different antibodies: MECA-79 (BD Pharmingen), HECA-452 (BD Pharmingen), CSLEX (ATCC) and PEN5 (Beckman Coulter). Binding of MECA-79 and HECA-452 was detected with goat FITC-conjugated anti-rat IgM (Jackson ImmunoResearch Laboratories). Binding of CSLEX and PEN5 was detected with goat FITC-conjugated anti-mouse IgM (Jackson ImmunoResearch Laboratories). As controls, an FITC-conjugated, isotype-matched, rat IgM antibody (anti-KLH, eBioscience) or PBS was substituted for the primary antibody. Cell nuclei were visualized by Hoechst 33342 staining (Molecular Probes). Sixteen samples of human uterus and 10 samples of mouse uterus were analyzed in 8 experiments.

Immunoblotting

Immunoblotting methods were as published. Genbacev et al. (1997) *Science* 277:1669–72. In all cases, equal amounts of protein were analyzed. The antibodies were those used for immunolocalization, except that antiCD62L (R&D Systems) was used to analyze L-selectin expression. Uterine expression of selectin oligosaccharide ligands was analyzed in 16 samples. Control blots of the same samples were incubated in PBS or an irrelevant rat IgM antibody (anti-KLH; eBioscience) rather than the primary antibody. Human trophoblast L-selectin expression was analyzed using first-trimester cytotrophoblast lysates (n=10 isolates of 5–7 placentas; 8–11 weeks) and cytotrophoblast columns dissected from explants (see FIG. 3a; n=48 explants from 12 placentas). Jurkat and neutrophil lysates were analyzed in parallel. Control blots of the same samples were incubated in PBS, rather than the primary antibody. Both experiments were done three times.

Preparation of Selectin Ligand-coated Beads

Neoglycolipids were prepared by reductive amination of dipalmitoyl phosphatidylacetaldehyde with the aminoethyl glycoside of either sLe$^x$ or 6-sulfo sLe$^{x\ 30}$ and dissolved in methanol (1 µg/µl). Blue 4-µm polystyrene latex beads (Interfacial Dynamics Corporation) were washed three times with ethanol, then resuspended in this solvent (1.2×10$^8$ beads/200 µl). Twenty-five micrograms of glycolipid was added, and the mixture was evaporated under nitrogen. Coated beads were washed three times in 1% BSA/PBS, then incubated with 3% BSA/PBS (2 h, room temperature). The beads were resuspended in 1 ml of 1% BSA/culture medium. Control beads were coated with phosphatidyl choline or used without coating.

Binding of Beads to Trophoblasts

Forty-eight first-trimester villous explant cultures were established (4 from 12 placentas; 2 experiments). After 24 h, the culture medium was removed, and 200 µl of a suspension of 2.4×10$^7$ beads in medium was added. Six explants were incubated with either experimental or control beads. Six other explants were pre-incubated with DREG-56 (30 min), then washed three times with medium before adding 6-sulfo sLe$^x$-coated beads. The explants were placed inside an incubator on a platform shaker (1 h; 20 cycles/min). Afterwards, bead suspensions were aspirated and explants were fixed in 3.8% paraformaldehyde (1 h, room temperature), washed three times in PBS (4° C.), and examined with a stereomicroscope. The same methods and controls were used to assess bead binding to hatched mouse blastocysts in culture (n=68 embryos; 2 experiments).

Results

Figure 1C:
Figure 1D:
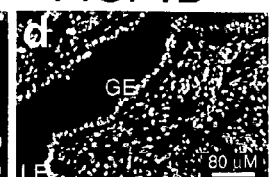

To determine whether selectin ligands were present at appropriate times and locations to function in blastocyst adhesion to the uterus, we studied their expression at the maternal-fetal interface with antibodies that bind sulfated oligosaccharides that interact with L-selectin. We found that tissue sections of uterine biopsies obtained from patients on days 6 and 19 of the menstrual cycle reacted with the MECA-79 antibody, which recognizes carbohydrate epitopes on all L-selectin ligands (particularly SO$_3$→6 GlcNAc). Yeh et al. (2001) *Cell* 105, 957–69. (2001). On day 6, when the uterus was not receptive, MECA-79 reactivity localized to the surface of glandular and luminal epithelia (FIGS. 1a,b). Staining was patchy and weaker than the more intense immunoreactivity observed when the uterus was receptive (day 19; FIGS. 1c,d). We also stained the same samples with the HECA-452 antibody, which reacts with sLe$^x$ (Siaα2→3Galβ1→4[Fucα1→3]GlcNAc) and related structures, including 6-sulfo sLe$^x$ (Siaα2→3Galβ1→4[Fucα1→3][SO$_3$→6]GlcNAc), 6'-sulfo sLe$^x$ (Siaα2→3[SO$_3$→6]Galβ1→4[Fucα1→3]GlcNAc) and 6',6-disulfo sLe$^x$ (Siaα2→3[SO$_3$→6]Galβ1→4[Fucα1→3][SO$_3$→6]GlcNAc). Mitsuoka et al. *Biochem Biophys Res Commun* 230, 546–51. (1997).

Figure 1E:
Figure 1F:
Figure 1G:
Figure 1H:
Figure 1I:
Figure 1J:
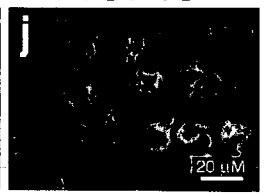

Again, antibody reactivity, limited to luminal and glandular epithelial cells, was weaker on day 6 and stronger on day 19 of the cycle. In agreement with the findings of Hey and Aplin (*Glycoconj J* 13, 769–79 (1996)), uterine staining with the CSLEX-1 antibody, which detects sLe$^x$ (Mitsuoka, et al. *Biochem Biophys Res Commun* 230, 546–51. (1997)), followed the same pattern. Staining with the PEN5 antibody, which recognizes a keratin sulfate-related lactosamine L-selectin ligand (Andre et al. *Proc Natl Acad Sci USA* 97, 3400–5. (2000)), also increased on uterine epithelium during the window of receptivity (compare FIGS. 1e and g) and shifted to decidual cells once pregnancy was established (FIG. 1i). Additionally, as previously reported, uterine CD45-positive large granule leukocytes expressed this carbohydrate epitope. Calatayud et al. *Int Immunol* 8, 1637–42. (1996). Analyses of samples later in gestation showed that staining with all four antibodies was lost during the second trimester, a situation that persisted until birth. The only exception was PEN5 staining, which was retained on large granule leukocytes.

We also examined uterine patterns of selectin oligosaccharide ligand expression in mice because data on selectin function has been obtained in knockout animals. In the nonreceptive uterus (day 1), the epithelium exhibited very little or no immunoreactivity when stained with HECA-452 (FIG. 1l) or MECA-79. As the uterus became receptive (day 4), the luminal and glandular epithelial cells (and portions of the stromal compartment) stained with the HECA-452 antibody (FIG. 1n), but failed to react with MECA-79. Together, these results suggest that different sets of L-selectin oligosaccharide ligands are expressed in the receptive uteri of humans and mice. Lack of expression of the MECA-79-reactive selectin oligosaccharide ligands by mouse uterine epithelia may explain why mice without L-, P- and E-selectin reproduce. Frenette and Wagner *Thromb Haemost* 78, 60–4. (1997). This difference could also explain why the uterine epithelium appears to play a more important role in human implantation than in the mouse, where the luminal epithelial cells adjacent to the blastocyst undergo apoptosis and are phagocytized by trophoblasts. Carson, D. D. *Dev Biol* 223, 217–37. (2000); and Enders *Semin Reprod Med* 18, 255–63 (2000).

Figure 1K:
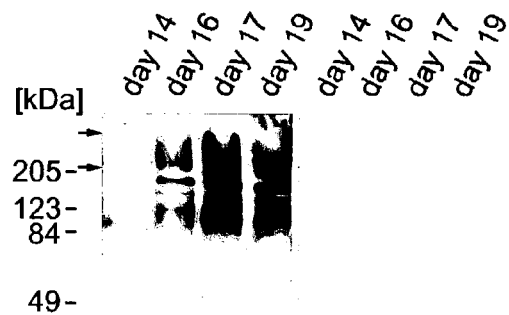
Figure 1L:
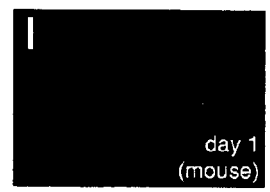
Figure 1M:
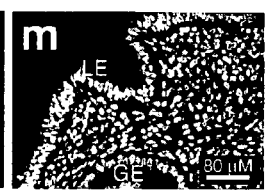
Figure 1N:
Figure 1O:
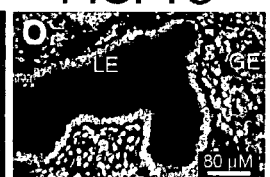

Immunoblot analyses with MECA-79 confirmed upregulation of selectin oligosaccharide ligands as the window of human receptivity opens (3–5 days after ovulation; FIG. 1k). On day 14 (day of ovulation), a few faint immunoreactive bands were detected. On day 16, strong immunoreactivity was observed in four areas—a diffuse, high molecular mass band(s) in the stacking gel and at least three bands in the ~120–200 kDa region of the running gel. The diffuse bands are expected for the highly O-glycosylated proteins known to function as selectin ligands. The increase in MECA-79 reactivity observed on days 17 and 19 over that on days 14 and 16 suggests that the concentration of selectin ligands increases in the days immediately following ovulation. No immunoreactivity was observed when a replica of the same lysates was incubated with an unrelated, rat isotype-matched control secondary antibody (anti-KLH [keyhole limpet hemocyanin]). Lysates of the same samples were also subjected to immunoblot analyses using HECA-452, CSLEX-1 or PEN5. These antibodies reacted primarily with the very high-molecular-mass component(s) in the stacking gel. Together, these results suggest that uterine expression of specialized carbohydrate structures that support selectin-mediated adherence is dramatically upregulated as the uterus becomes receptive.

Figure 2A:
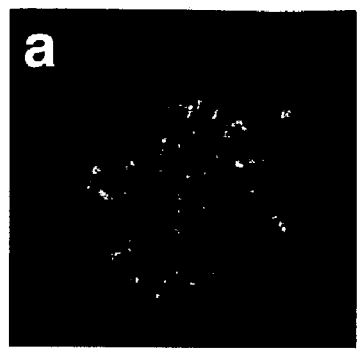
FIGS. 2A–F depict results showing that placental trophoblasts express L-selectin in situ. MΦ, macrophage; STB, syncytiotrophoblast; iCTB, invasive cytotrophoblast.
Figure 2B:
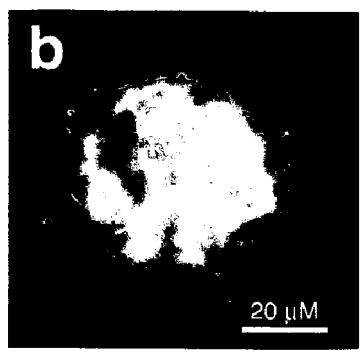
Figure 2C:
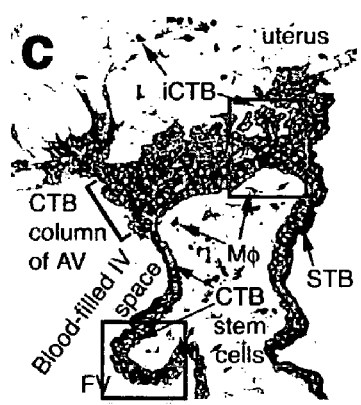
Figure 2D:
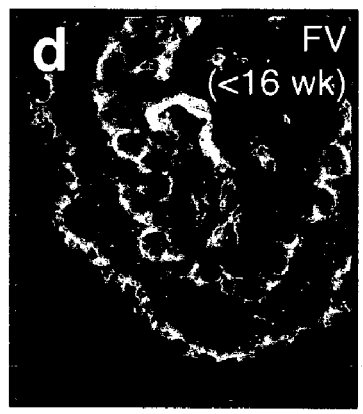
Figure 2E:
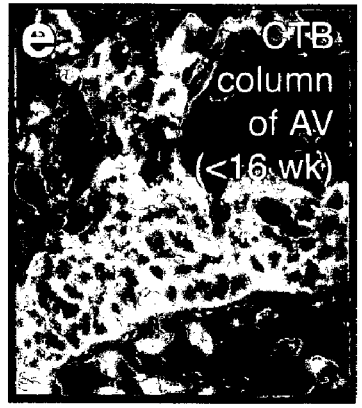

Immediately after they hatched, we stained mouse blastocysts with FITC-conjugated anti-L-selectin. Before permeabilization, a punctate staining pattern was observed in association with the surface trophectoderm (FIG. 2a). After permeabilization, the staining pattern was diffuse (FIG. 2b). Embryos incubated with an irrelevant, control FITC-conjugated IgG did not stain. Expression of L-selectin by human embryos has been reported. Campbell et al. *Hum Reprod* 10, 1571–8. (1995). Additionally, we analyzed L-selectin expression in tissue sections of the human maternal-fetal interface, which contained anchoring villi that attach to the uterine wall, and floating villi, which float in maternal blood. These villi contain trophoblasts in all stages of differentiation, including aggregates of fetal cytotrophoblasts (cell columns), in the blood-filled intervillus space. These cytotrophoblasts attach to the uterine wall (diagrammed in FIG. 2c) and intravasate maternal blood vessels. Between 6 and 16 weeks of gestation, cytotrophoblast stem cells (FIG. 2d), cytotrophoblasts in cell columns, and invasive cytotrophoblasts (FIG. 2e) strongly reacted with an antibody that recognizes the extracellular domain of L-selectin. The pattern of reactivity was indicative of antibody binding to cell-surface L-selectin.

Figure 2F:
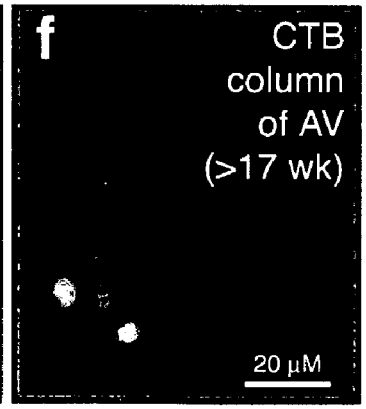

Overlying syncytiotrophoblasts also stained, as did macrophages in the villus stromal cores. To establish that trophoblast L-selectin staining was not due to adsorption of shed L-selectin from blood, antibodies that recognized the carboxyl terminus of the molecule were also used in immunolocalization experiments. The same populations of cells stained with both antibodies. But from 17 weeks of gestation to term, none of the trophoblast populations stained with either antibody, although macrophages continued to react with anti-L-selectin (FIG. 2f). Because the selectins have been shown to have overlapping functions in mediating leukocyte rolling and tethering, we also examined human trophoblast expression of P- and E-selectin. Anti-P-selectin stained first- and second-trimester syncytiotrophoblasts, and anti-E-selectin failed to react with any of the samples.

Figure 3A:
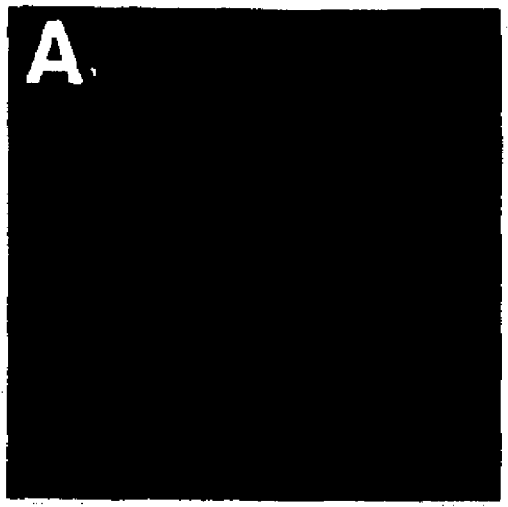
FIGS. 3A–D depict results showing that human trophoblasts express L-selectin in situ.
Figure 3B:
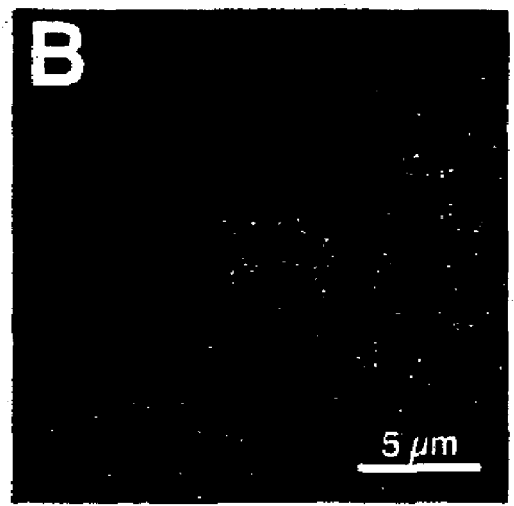
Figure 3C:
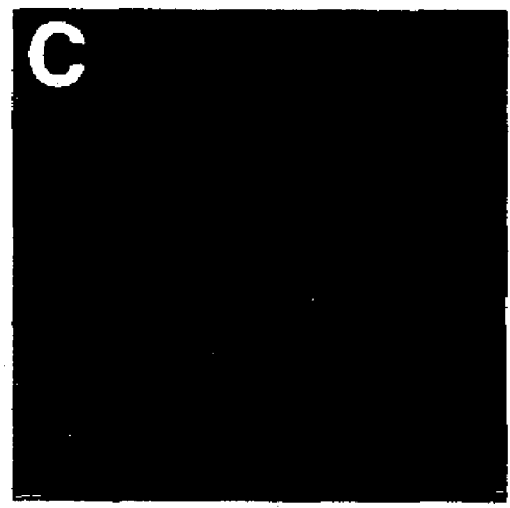
Figure 3D:
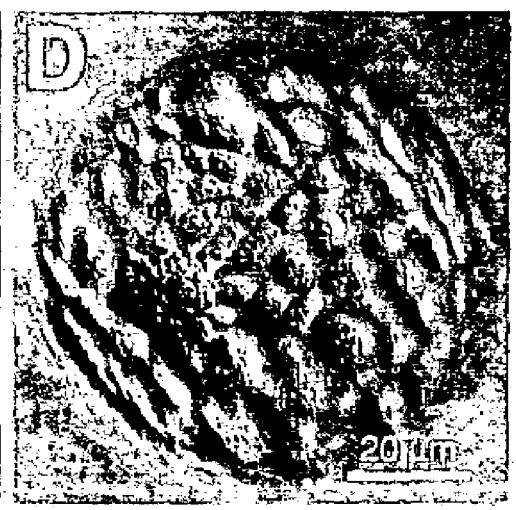

We asked whether the trophectoderm of implantation-competent human embryos expresses L-selectin. We stained human blastocysts, without permeabilization, using FITC-conjugated anti-L-selectin. Before the embryo hatched from the zona pellucida, L-selectin expression was either weak and diffuse or absent (FIG. 3A). After hatching, strong staining was observed in association with the trophectoderm (FIG. 3B) over the entire embryo surface (FIG. 3C) seen by phase-contrast microscopy in FIG. 3D.

To support our in situ observations, we characterized human trophoblast L-selectin expression in vitro using two culture systems that model cytotrophoblast differentiation along the pathway that leads to uterine attachment and invasion. In the first, an organ culture model, explanted anchoring villi are cultured on Matrigel-coated wells; villi attach to the extracellular matrix via the remnants of severed cytotrophoblast columns that subsequently give rise to invasive cytotrophoblasts. Sections of explants cultured for 72 h were stained with anti-L-selectin.

Figure 4A:
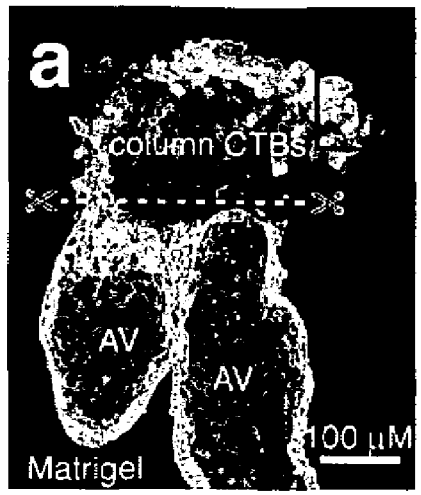
FIGS. 4A–D depict results showing that human trophoblasts express L-selectin in vitro.
Figure 4B:
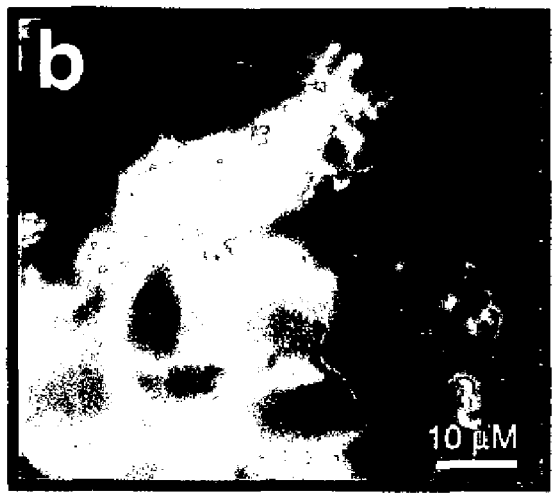
Figure 4C:
Figure 4D:
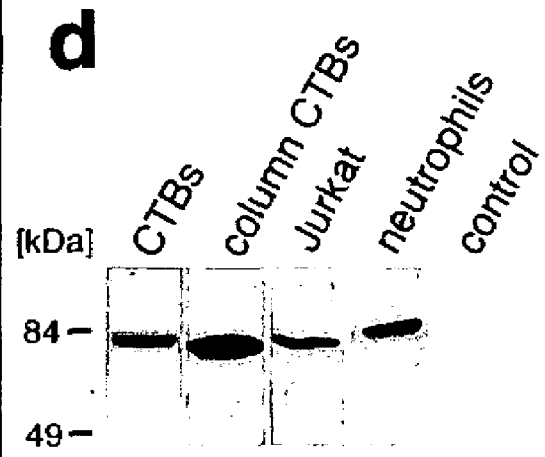

The pattern of antibody reactivity was very similar to that observed in situ; cytotrophoblast stem cells within the villi and column cytotrophoblasts that invaded the Matrigel stained, as did the syncytial surface (FIG. 4a). At higher magnification, the pattern of cytotrophoblast staining was indistinguishable from that of Jurkat cells that express L-selectin (Giblin et al. *J Immunol* 159, 3498–507. (1997)) (compare FIGS. 4b and 4c). In a second in vitro model, purified cytotrophoblast stem cells plated on Matrigel differentiate to invasive cells over 48–72 h. After 48 h these cells also reacted with anti-L-selectin. To confirm antigen identity, lysates prepared from isolated cytotrophoblasts and the columns dissected from explants (see FIG. 4a) were analyzed by immunoblotting samples that were separated on 10% polyacrylamide gels. These samples contained a broad ~75–90 kDa band (FIG. 4d). Jurkat and neutrophil lysates contained the same bands. Together, these data indicate that trophoblast upregulation of L-selectin expression occurs concomitantly with the opening of the window of blastocyst attachment to the uterine epithelium and cytotrophoblast invasion of the underlying parenchyma.

Next we assessed the functional state of trophoblast L-selectin in vitro. Under shear stress, beads coated with either 6-sulfo sLe$^x$ (FIG. 5a) or sLe$^x$ bound to hatched mouse blastocysts; binding was inhibited by the addition of anti-L-selectin, and only a few uncoated beads bound (FIG. 5b). Beads coated with 6-sulfo sLe$^x$ also bound to explants of the human chorionic villous tree (FIG. 5c). They associated with cytotrophoblast column remnants of anchoring villi and with the syncytiotrophoblasts at the surfaces of the villi, i.e., the cells that express L-selectin in situ and in vitro. Beads that displayed sLe$^x$ also bound to villus explants, but in fewer numbers. This result is consistent with the finding that L-selectin binds more tightly to 6-sulfo sLe$^x$ than to sLe$^x$. Scudder et al. *Glycobiology* 4, 929–32. (1994). Very few control phosphatidyl choline-conjugated beads (FIG. 5d) bound to cytotrophoblast cell columns or syncytiotrophoblasts. Likewise, uncoated beads did not bind. Beads that displayed 6-sulfo sLe$^x$ did not adhere to explants pre-incubated with an antibody that blocks L-selectin function (FIG. 5e) suggesting that the binding was specific.

Figure 6A:
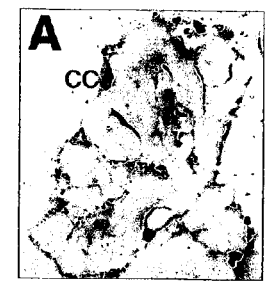
FIGS. 6A–K depict results showing that human trophoblasts use L-selectin to bind uterine epithelial oligosaccharide ligands.
Figure 6B:
Figure 6C:
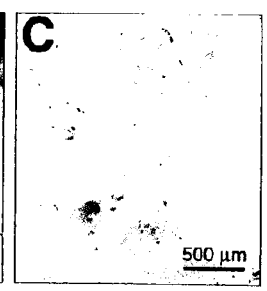
Figure 6D:
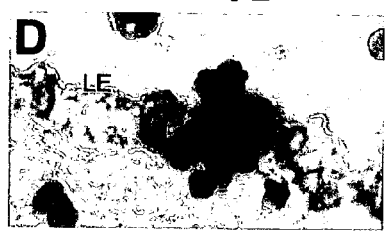
Figure 6E:
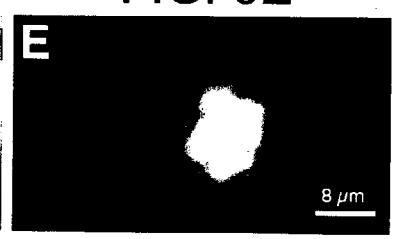
Figure 6F:
Figure 6G:
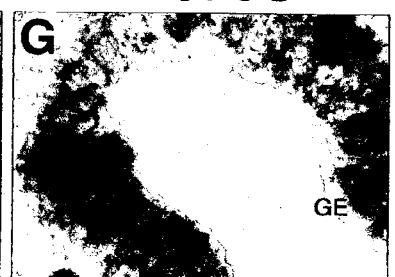
Figure 6H:
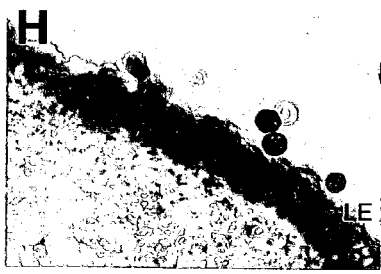
Figure 6I:
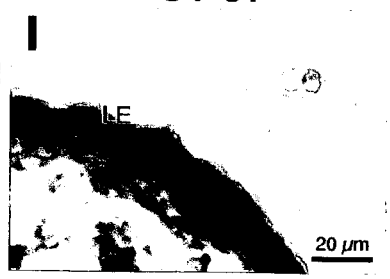
Figure 6J:
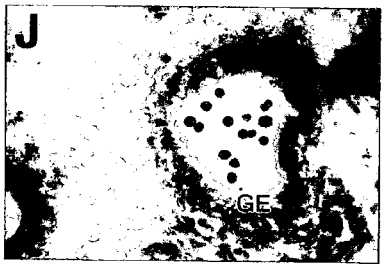
Figure 6K:

We also compared cytotrophoblast and Jurkat adhesion to tissue sections cut from uterine biopsies, a method that allows visualization of leukocyte adhesion through L-selectin to lymph node high endothelial venules (Stamper and Woodruff (1976) *J. Exp. Med.* 144:828) (FIG. 6, A–H). The data are quantified and summarized in FIG. 4I. Under shear stress, cytotrophoblasts, as single cells and clusters, primarily bound to the epithelial portion of the receptive (luteal phase) uterus, including the lumen (FIG. 6A). Adherent cells stained for L-selectin (FIG. 6B). Cytotrophoblasts also bound to glands and their contents (FIG. 6C). Adherence to both luminal (data not shown) and glandular (FIG. 6D) epithelium was inhibited by adding anti-L-selectin. Adherence was also inhibited when the tissue sections were preincubated with MECA-79 (FIG. 6I). Many fewer cytotrophoblasts bound to tissue sections of nonreceptive (follicular phase) biopsy specimens; epithelial adhesion was nearly absent (FIG. 6I). As a positive control, Jurkat binding to tissue sections of luteal phase uterine biopsies was tested. The cells preferentially adhered to epithelia (e.g., the luminal surface in FIG. 6E), and binding was inhibited by adding anti-L-selectin (FIG. 6F) or MECA-79 (FIG. 6I). Like cytotrophoblasts, the cells often adhered to glands (FIG. 6G) that contained MECA-79-reactive secretions (FIG. 6H).

The above data demonstrate a role for L-selectin function outside the blood-vascular system. This finding has several important implications for implantation and placentation. Shear stress, required for L-selectin-mediated adhesion through its specialized oligosaccharide ligands, is likely to be an important component of both processes. During implantation, apposition may be analogous to leukocyte transient tethering and rolling. Although the magnitude of shear stress at the surface of the receptive uterus is unknown, distractive forces are likely derived from several sources including fluid secretions and uterine contractions. Eytan et al. *Ann Biomed Eng* 27, 372–9. (1999); and Ijland et al. *Fertil Steril* 67, 492–496 (1997). During the early stages of placentation, cytotrophoblasts that invade and line maternal vessels experience the same shear stress as the resident vascular cells. Given the many and varied causes of infertility and early pregnancy loss, it seems likely that defects in the shear stress-activated selectin adhesion system at the maternal-fetal interface account for a portion of unexplained reproductive failures.

Trophoblast adhesion to the uterine wall is the requisite first step of implantation and, subsequently, placentation. At the maternal-fetal interface we investigated the expression of selectin adhesion systems that enable leukocyte capture from the bloodstream. On the maternal side, human uterine epithelial cells upregulated selectin oligosaccharide-based ligands during the window of receptivity. On the fetal side, human trophoblasts expressed L-selectin. This ligand-receptor system was functional, because beads coated with the selectin ligand 6-sulfo sLe$^x$ bound to trophoblasts, and trophoblasts bound to ligand-expressing uterine luminal epithelium in tissue sections. These results suggest that trophoblast L-selectin mediates interactions with the uterus and that this adhesion mechanism may be critical to establishing human pregnancy.

Our finding led us to question why mice without L-selectin reproduce. Frenette and Wagner (1997) *Thromb. Haemost.* 78:60. We immunostained implantation-competent mouse blastocysts for L-selectin and receptive murine uteri for its ligands (8; data not shown). Mouse trophectoderm expressed cell surface L-selectin. Receptive murine uterine luminal and glandular epithelium stained with HECA-452, which reacts with carbohydrate epitopes, but not with MECA-79, which requires sulfation for binding. The latter observation suggests that the sulfated carbohydrate structures that are the major L-selectin ligands in lymph nodes and receptive uterus (FIG. 1, C and K; FIG. 6I) are absent at the time of murine implantation.

Our finding of L-selectin functions outside the blood-vascular system has several important implications for implantation and placentation. Shear stress, required for optimal L-selectin-mediated adhesion in the vasculature, is likely an important component of both processes. Given the many and varied causes of infertility and early pregnancy loss, defects in the selectin adhesion system could account for a portion of unexplained reproductive failures, as well as deficient cytotrophoblast invasion, which is associated with pregnancy complications such as preeclampsia. Zhou et al. (1997) *J. Clin. Invest.* 99:2152. Our data also provide further insights into the highly unusual nature of trophoblasts. Our finding that these cells also share leukocyte adhesion mechanisms suggests that trophoblasts have characteristics of the hemangioblast stem cell population that gives rise to both blood cells and vessels. The implications include the possibility that interactions between L-selectin-bearing trophoblasts and PEN5-positive decidual natural killer cells could help target this unusual population of immune cells to the uterus. Together, our results suggest close links, at the molecular level, between processes that are key to reproductive, immune and vascular functions.

Example 2

Detection of L-selectin Ligand in Saliva

Figure 7:
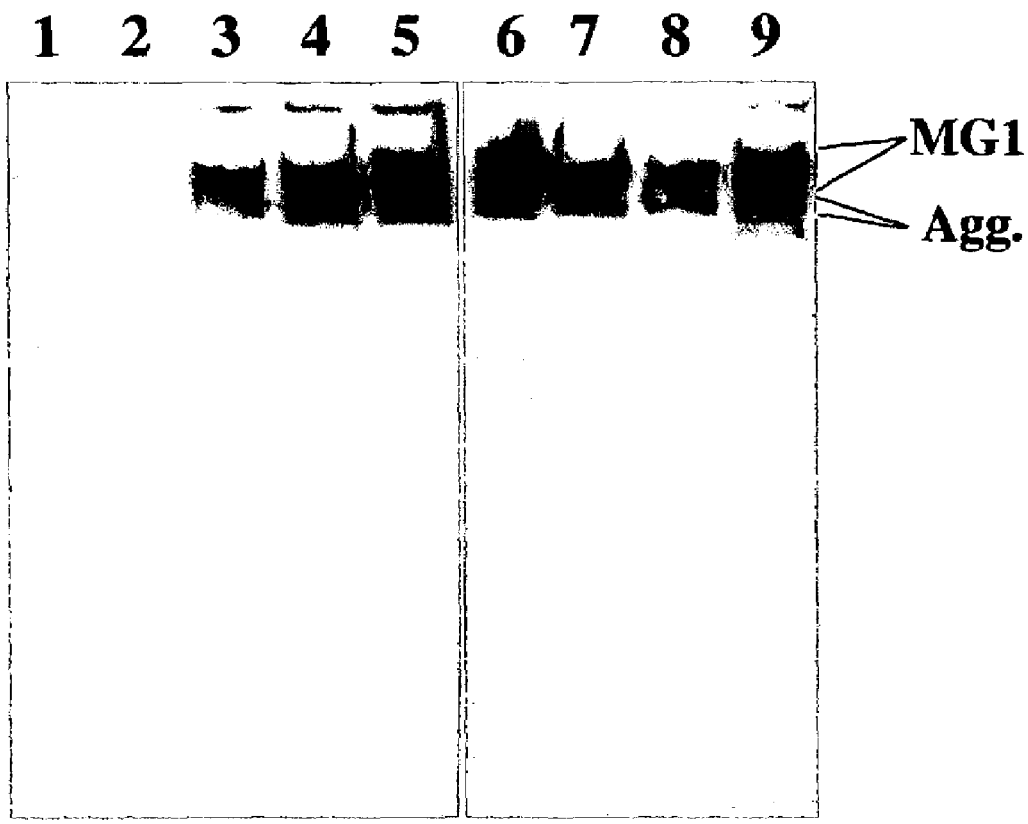
FIG. 7 depicts detection of L-selectin ligand in saliva.

L-selectin ligand was detected in saliva samples. The results are shown in FIG. 7. Salivary components express the MECA-79 (selectin ligand) epitope during the window of receptivity, pregnancy and lactation. Samples of whole saliva were collected by expectoration from a single donor during the nonreceptive (lanes 1–3) and receptive (lanes 4 and 5) stages of the cycle. Additional samples were obtained from the same donor during pregnancy (lanes 6 and 7) and lactation (lanes 8 and 9). The samples were separated by sodium dodecyl sulfate-polyacrylamide gel electrophoresis (SDS-PAGE) and stained with Alcian blue, which allowed visualization of the glycoprotein bands in each lane. A gel of the same samples was transferred to nitrocellulose and probed with the MECA-79 antibody, according to the methods described above. MECA-79 recognizes an important class of sulfated, high-affinity L-selectin ligands. As shown in FIG. 7, antibody reactivity dramatically increased as the window of receptivity approached. Likewise, antibody reactivity was high during pregnancy and lactation. MG1, the high-molecular-weight salivary mucin; Agg., the salivary agglutinin. Arrows indicate the top and the bottom of the stacking gel.

These results demonstrate that the L-selectin ligand can be easily detected in a biological fluid such as saliva, and that the levels are correlated with the phase of the menstrual cycle, pregnancy, and lactation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining the probability of success of implantation in a female human following an assisted reproductive technology or naturally achieved conception, the method comprising:

determining the level of an L-selectin ligand carbohydrate epitope that is produced by a uterine epithelial cell, and that is present in a biological sample from the female human, wherein the L-selectin ligand carbohydrate epitope comprises one or more carbohydrate epitopes selected from $SO_3 \rightarrow 6GlcNAc$, $sLe^x$ $(Sia\alpha 2 \rightarrow 3Gal\beta 1 \rightarrow 4[Fuc\alpha 1 \rightarrow 3]GlcNAc)$, 6-sulfo $sLe^x(Sia\alpha 2 \rightarrow 3Gal\beta 1 \rightarrow 4[Fuc\alpha 1 \rightarrow 3][SO_3 \rightarrow 6]GlcNAc)$, 6'-sulfo $sLe^x(Sia\alpha 2 \rightarrow 3[SO_3 \rightarrow 6]Gal 1 \rightarrow 4[Fuc\alpha 1 \rightarrow 3]GlcNAc)$, and 6',6-disulfo $sLe^x$ $(Sia\alpha 2 \rightarrow 3[SO_3 \rightarrow 6]Gal\beta 1 \rightarrow 4[Fuc\alpha 1 \rightarrow 3][SO_3 \rightarrow 6]GlcNAc)$;

comparing the level to a standard; and determining the probability of success of implantation following an assisted reproductive technology or naturally achieved conception based on the level of an L-selectin ligand carbohydrate epitope produced by the uterine epithelial cell, wherein an increase in the level of the L-selectin ligand carbohydrate epitope, compared to a control level, indicates an increased probability of success of implantation.

2. The method of claim 1, wherein the biological sample is selected from the group consisting of a uterine biopsy sample, a uterine fluid sample, a vaginal fluid sample, saliva, and maternal blood.

3. The method of claim 1, wherein the assisted reproductive technology is selected from the group consisting of in vitro fertilization, embryo transfer, gamete intrafallopian transfer, tubal embryo transfer, intracytoplasmic sperm injection, and intrauterine insemination.

4. The method of claim 1, wherein the L-selectin ligand carbohydrate epitope is detected with an immunological assay using an antibody specific for the L-selectin ligand carbohydrate epitope.

5. The method of claim 4, wherein the antibody is detectably labeled.

6. The method of claim 1, wherein the L-selectin ligand carbohydrate epitope is sulfated.

* * * * *

UNITED STATES PATENT AND TRADEMARK OFFICE
CERTIFICATE OF CORRECTION

PATENT NO.        : 7,175,990 B2                                    Page 1 of 1
APPLICATION NO.   : 10/374318
DATED             : February 13, 2007
INVENTOR(S)       : Susan J. Fisher et al.

It is certified that error appears in the above-identified patent and that said Letters Patent is hereby corrected as shown below:

Col. 22,
In Claim 1, please replace line 26:

"GlcNAc), 6'-sulfo sLe$^x$ (Siaa2→3[SO$_3$→6]Gal→4"

With the following line:

-- GlcNAc), 6'-sulfo sLe$^x$ (Siaa2→3[SO$_3$→6]Galß1→4 --.

Signed and Sealed this

Fifth Day of June, 2007

JON W. DUDAS
*Director of the United States Patent and Trademark Office*